United States Patent
Overmyer et al.

(10) Patent No.: US 10,357,270 B2
(45) Date of Patent: Jul. 23, 2019

(54) RESISTING TORQUE IN ARTICULATING SURGICAL TOOLS

(71) Applicant: Ethicon LLC, Guaynabo, PR (US)

(72) Inventors: Mark D. Overmyer, Cincinnati, OH (US); Robert L. Koch, Jr., Cincinnati, OH (US); Jeffrey S. Swayze, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 221 days.

(21) Appl. No.: 15/422,740

(22) Filed: Feb. 2, 2017

(65) Prior Publication Data

US 2018/0214168 A1    Aug. 2, 2018

(51) Int. Cl.
*A61B 17/00* (2006.01)
*A61B 17/28* (2006.01)
(Continued)

(52) U.S. Cl.
CPC .......... *A61B 17/32* (2013.01); *A61B 17/072* (2013.01); *A61B 17/28* (2013.01); *A61B 17/295* (2013.01);
(Continued)

(58) Field of Classification Search
CPC ....... A61B 17/32; A61B 34/30; A61B 17/072; A61B 17/28; A61B 17/29; A61B 17/295;
(Continued)

(56) References Cited

U.S. PATENT DOCUMENTS

2010/0030023 A1*  2/2010  Yoshie .............. A61B 1/00147
                                                        600/117
2014/0200612 A1   7/2014  Weir et al.
(Continued)

FOREIGN PATENT DOCUMENTS

EP          2151184 A1      2/2010
WO     WO-2014151621 A1     9/2014
(Continued)

OTHER PUBLICATIONS

International Search Report and Written Opinion for International Application No. PCT/IB2018/050560 dated May 11, 2018 (12 pages).
(Continued)

*Primary Examiner* — Katrina M Stransky
(74) *Attorney, Agent, or Firm* — Mintz Levin Cohn Ferris Glovsky and Popeo, P.C.

(57) ABSTRACT

Various exemplary systems, devices, and methods are provided for resisting torque in articulating surgical tools. In general, a surgical tool can include an elongate shaft having at a distal end thereof an end effector configured to engage tissue. The end effector can be configured to articulate relative to the elongate shaft. The surgical tool can include a cutting element configured to translate longitudinally along the end effector to cut the engaged tissue. When the end effector is articulated, the longitudinal translation of the cutting element along the end effector exerts a torque force on the end effector that urges the end effector away from its current angled orientation. The surgical tool can be configured to have a corrective tension or force applied thereto that counteracts the torque force.

20 Claims, 11 Drawing Sheets

(51) Int. Cl.
| | |
|---|---|
| *A61B 17/29* | (2006.01) |
| *A61B 17/32* | (2006.01) |
| *A61B 17/072* | (2006.01) |
| *A61B 17/295* | (2006.01) |
| *A61B 34/30* | (2016.01) |
| *A61B 18/14* | (2006.01) |
| *A61B 90/00* | (2016.01) |

(52) U.S. Cl.
CPC ...... *A61B 17/320016* (2013.01); *A61B 34/30* (2016.02); *A61B 2017/00017* (2013.01); *A61B 2017/00398* (2013.01); *A61B 2017/07264* (2013.01); *A61B 2017/07285* (2013.01); *A61B 2017/293* (2013.01); *A61B 2017/2927* (2013.01); *A61B 2017/320093* (2017.08); *A61B 2017/320094* (2017.08); *A61B 2018/1452* (2013.01); *A61B 2034/305* (2016.02); *A61B 2090/064* (2016.02); *A61B 2090/066* (2016.02); *A61B 2090/067* (2016.02)

(58) Field of Classification Search
CPC ............ A61B 17/320016; A61B 18/14; A61B 2034/305; A61B 2090/064; A61B 2090/066; A61B 2090/067; A61B 2018/146; A61B 2018/1452
See application file for complete search history.

(56) References Cited

U.S. PATENT DOCUMENTS

2014/0263542 A1* 9/2014 Leimbach ............ A61B 17/064
  227/175.2
2014/0343569 A1  11/2014 Turner

FOREIGN PATENT DOCUMENTS

WO   WO-2014151952 A1   9/2014
WO   WO-2016186999 A1   11/2016

OTHER PUBLICATIONS

U.S. Appl. No. 15/200,283 entitled "Methods, Systems, and Devices for Initializing a Surgical Tool" filed Jul. 1, 2016.

U.S. Appl. No. 15/237,648 entitled "Methods, Systems, and Devices for Causing End Effector Motion With a Robotic Surgical System" filed Aug. 16, 2016.

U.S. Appl. No. 15/237,653 entitled "Methods, Systems, and Devices for Controlling a Motor of a Robotic Surgical Systems" filed Aug. 16, 2016.

* cited by examiner

RESISTING TORQUE IN ARTICULATING SURGICAL TOOLS

FIELD

Methods and devices are provided for robotic surgery, and in particular for resisting torque in articulating surgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, systems, devices, and methods for resisting torque in articulating surgical tools are provided.

In one aspect, a surgical system is provided that in one embodiment includes a surgical tool including an elongate shaft having an end effector at a distal end thereof. The surgical tool also includes a rod configured to move to selectively angularly orient the end effector at an angle relative to the elongate shaft. The movement of the rod is configured to be driven by a motor providing a torque force to the surgical tool. The surgical system also includes a controller configured to determine an amount of corrective force based on the angle and the torque force, and the controller is configured to apply the determined corrective force to the rod.

The surgical system can vary in any number of ways. For example, the surgical tool can include a cutting element configured to translate along the end effector to cut tissue engaged by the end effector, and the controller can be configured to cause the determined corrective force to be applied to the rod during the translation of the cutting element. For another example, the surgical system can include a memory storing a lookup table therein, the lookup table can correlate each of a plurality of articulation angles and a plurality of motor torque forces to corrective forces to apply to the rod, and the controller can be configured to determine the amount of corrective force via the lookup table. For yet another example, the controller can be configured to determine the angle at which the end effector is angularly oriented relative to the elongate shaft. For another example, the end effector can be configured to pivot at a joint relative to the elongate shaft to effect the angular orientation of the end effector relative to the elongate shaft, and the rod can extend through the joint. For still another example, the controller can be included in a robotic surgical system configured to releasably couple to the surgical tool.

For another example, the surgical system can include a tool driver of a robotic surgical system that includes the motor, and the surgical tool can be configured to releasably operatively couple to the tool driver. In at least some embodiments, the robotic surgical system can include the controller, and the controller cam be in operative communication with the tool driver.

In another embodiment, a surgical system is provided that includes a surgical tool including an elongate shaft, an end effector coupled to a distal end of the elongate shaft, a cutting element configured to translate along the end effector to cut tissue engaged by the end effector, and a rod configured to move to articulate the end effector at an angle relative to the elongate shaft in response to a first force provided to the surgical tool by a robotic surgical system configured to releasably couple to the surgical tool. The surgical system also includes a controller configured to cause adjustment of the first force provided to the surgical tool by the robotic surgical system during the translation of the cutting element and thereby counteract a second force caused by the translation of the cutting element along the end effector.

The surgical system can have any number of variations. For example, the cutting element can be configured to translate along the end effector in response to a third force provided to the surgical tool by the robotic surgical system, and the controller can be configured to determine an amount of the adjustment of the first force based on the third force and on the angle at which the end effector is articulated relative to the elongate shaft. In at least some embodiments, the surgical system can include a memory storing a lookup table therein that correlates amounts of the second force to each of a plurality of angles at which the end effector can be articulated relative to the elongate shaft and each of a plurality of third forces that can be provided to the surgical tool by the robotic surgical system to cause the translation of the cutting element, and the controller determining the amount of the adjustment of the first force can include looking up in the lookup table the angle at which the end effector is articulated relative to the elongate shaft and looking up in the lookup table the third force being provided to the surgical tool by the robotic surgical system.

For another example, the surgical system can include a memory storing a lookup table therein, and the controller can be configured to access the lookup table and thereby determine an amount of the adjustment of the first force. For yet another example, the robotic surgical system can include a motor configured to provide the first force to the surgical tool. For still another example, the controller can be included in the robotic surgical system.

In another aspect, a surgical method is provided that in one embodiment includes applying an amount of force to a surgical tool and thereby cause an end effector of the surgical tool to articulate at an angle relative to an elongate shaft having the end effector at a distal end thereof, and, with the end effector articulated, causing a cutting element to translate along the end effector. The surgical method also includes, during the translation of the cutting element, changing the amount of force being applied to the surgical tool while maintaining the angle at which the end effector is articulated relative to the elongate shaft.

The surgical method can have any number of variations. For example, the translation of the cutting element along the end effector can exert a second amount of force on the surgical tool, and changing the amount of force being applied to the surgical tool can counteract the second amount of force to allow the surgical tool to maintain the angle at which the end effector is articulated relative to the elongate shaft.

For another example, the translation of the cutting element can be caused by applying a second amount of force to the surgical tool, and the amount of force being applied to the surgical tool can be changed based on the angle at which the end effector is articulated relative to the elongate shaft and based on the second amount of force being applied to the surgical tool. In at least some embodiments, the surgical tool can be releasably and replaceably coupled to a robotic surgical system, and the robotic surgical system can apply the amount of force to the surgical tool and can apply the second amount of force to the surgical tool.

For yet another example, the surgical tool can be releasably and replaceably coupled to a robotic surgical system, and the robotic surgical system can apply the amount of force to the surgical tool and can change the amount of force being applied to the surgical tool.

BRIEF DESCRIPTION OF THE DRAWINGS

The invention will be more fully understood from the following detailed description taken in conjunction with the accompanying drawings, in which.

DETAILED DESCRIPTION

Figure 1:
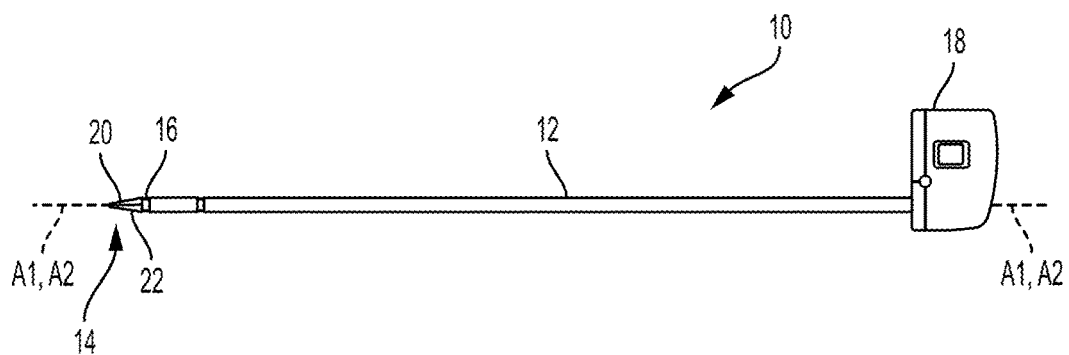
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary systems, devices, and methods are provided for resisting torque in articulating surgical tools. In general, a surgical tool can include an elongate shaft having at a distal end thereof an end effector configured to engage tissue. The end effector can be configured to articulate relative to the elongate shaft, e.g., angularly orient relative to a longitudinal axis of the elongate shaft, which may help the end effector access and securely engage the tissue. The surgical tool can include a cutting element configured to translate longitudinally along the end effector to cut the engaged tissue. When the end effector is articulated, e.g., is angled at a non-zero angle relative to the shaft's longitudinal axis, the longitudinal translation of the cutting element along the end effector exerts a torque force on the end effector that urges the end effector away from its current angled orientation, e.g., urges the end effector toward a substantially zero angle position in which it is substantially aligned with the shaft's longitudinal axis. However, articulating movement of the end effector from its current angled orientation during cutting of the tissue may cause the end effector to undesirably shift in position relative to the engaged tissue such that the tissue is not cut at a proper location, and/or may cause the end effector to undesirably press against matter (e.g., an adjacent body structure, another surgical tool, etc.) in the patient's body that may cause harm to the matter and/or the end effector. The surgical tool can be configured to have a corrective tension or force applied thereto that counteracts the torque force, thereby preventing the end effector from moving from its articulated angle during the translation of the cutting element. The corrective force can be applied to the surgical tool without use of a mechanical locking mechanism that locks the end effector in its articulated position during cutting element translation, which may simplify manufacture of the surgical tool and/or may allow more space for other and/or larger tool components since a locking mechanism need not be present.

The surgical tool can be configured to releasably couple to a robotic surgical system (also referred to herein as a "surgical robot") configured to control a variety of movements and actions associated with the surgical tool. The robotic surgical system can be configured to provide the corrective force to the surgical tool. The robotic surgical system can also be configured to determine an amount of the corrective force to apply to the surgical tool in real time with the cutting element's translation, which may help ensure that the force exerted by the cutting element's movement is counteracted without over-correction or under-correction. The amount of the corrective force can be determined based on the end effector's current angle of articulation and on a force being applied to the surgical tool (e.g., applied by the robotic surgical system) to cause the cutting element's longitudinal translation along the end effector. The current angle of articulation and the force being applied to cause the cutting element translation can be correlated to predetermined corrective forces to determine the corrective force to be applied to the surgical tool.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components (e.g., gears and/or actuators) configured to control the operation various features associated with the end effector 14 any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This tray allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

The wrist 16 can have any of a variety of configurations. Exemplary embodiments of a wrist of a surgical tool and of effecting articulation at the wrist are described in International Pat. Pub. No. WO 2014/151952 entitled "Compact Robotic Wrist" filed on Mar. 13, 2014, International Pat. Pub. No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

Figure 2:
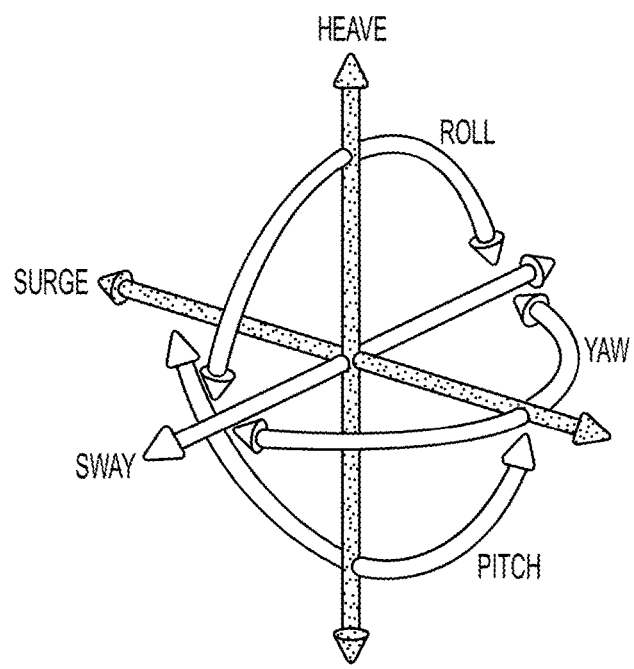
FIG. 2 is a graphical representation of terminology associated with six degrees of freedom.

FIG. 2 illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 2, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The movement of the end effector 14 in this illustrated embodiment includes articulating movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1. The movement of the end effector 14 in this illustrated embodiment also includes rotational movement of the end effector 14 in which the end effector 14 rotates about its longitudinal axis A2, either with or without corresponding rotation of the shaft 12 about its longitudinal axis A1.

The surgical tool 10 can include one or more actuation shafts configured to facilitate movement of the end effector 14. Each of the one or more actuation shafts can extend along the shaft 12 (e.g., in an inner lumen thereof) and can be operatively coupled to the housing 18 and to the end effector 14. In this way, a tool driver coupled to the housing 18 can be configured to provide input to the surgical tool 10 via the tool housing 18 and thereby actuate the one or more actuation shafts to cause movement of the end effector 14.

Figure 3:
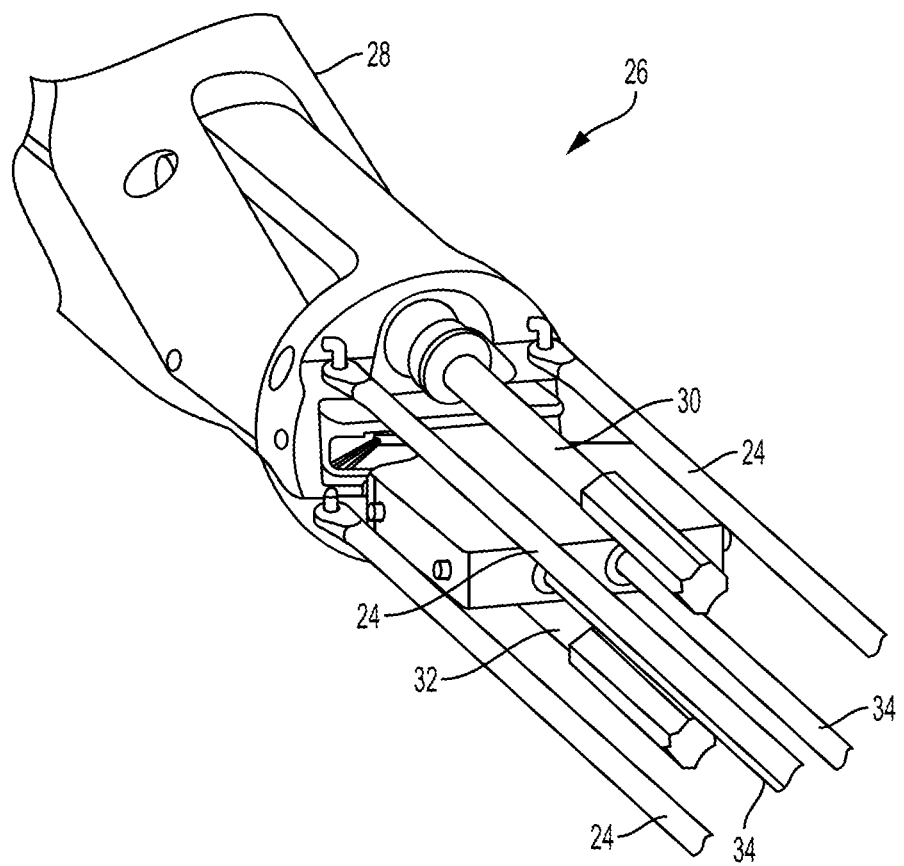
FIG. 3 is a perspective view of a wrist portion of another embodiment of a surgical tool.

FIG. 3 illustrates one embodiment of a surgical tool, such as the tool 10 of FIG. 1, that includes one or more actuation shafts 24 configured to be actuated to cause movement of an end effector 36 (see FIG. 4) operatively coupled thereto. FIG. 3 illustrates a distal end of the actuation shafts 24 extending from a wrist 26 located just proximal of the end effector 36. The wrist 26 can allow for fine movements and angulation of the end effector 36 relative to the proximal end of an elongate shaft 28 to which the end effector 36 is coupled. In this illustrated embodiment, the wrist 26 includes three actuation shafts 24, each in the form of a rod, that are spaced around a perimeter of the wrist 26. When actuated (e.g., pushed, pulled, rotated), the actuation shafts 24 will cause articulation of the end effector (e.g., movement up, down, left, right, and combinations thereof) relative to the shaft 28. The actuation shafts 24 are configured to be operatively coupled to a tool driver, via a tool housing of the surgical tool as discussed herein, to cause selective proximal and distal movement of selected one or more of the actuation shafts 24 to cause selected articulation of the end effector 36.

The wrist 26 also includes an upper rotary driver 30 that when actuated can cause a pair of jaws of the end effector 36 to close. The upper rotary driver 30 is configured to be operatively coupled to the tool driver, via the tool housing, to cause rotation of the upper rotary driver 30 and hence closure of the end effector 36. The wrist 26 also includes a lower rotary driver 32 that when actuated can cause movement of a sled relative the end effector 36, e.g., can cause the sled to longitudinally translate along the end effector 36. The sled translating along the end effector 36 can cause a cutting element to translate along the end effector 36 to cut tissue engaged by the end effector 36, as discussed further below. The lower rotary driver 32 is configured to be operatively coupled to the tool driver, via the tool housing, to cause rotation of the lower rotary driver 32 and hence translation of the sled along the end effector 36. The wrist 26 can also include at least one linear pull cable 34 that when actuated moves linearly in a proximal direction to cause rapid close of the end effector 36, e.g., rapid closure of the jaws. The at least one linear pull cable 34 is configured to be operatively coupled to the tool driver, via the tool housing, to cause the proximal movement thereof. Exemplary embodiments of the tool driver and operatively coupling the tool driver to actuation members such as the actuation shafts 24, rotary drivers 30, 32, and linear pull cables 34 are further described in U.S. patent application Ser. No. 15/237,648 entitled "Methods, Systems, And Devices For Causing End Effector Motion With A Robotic Surgical System" filed on Aug. 16, 2016, which is hereby incorporated by reference in its entirety.

Figure 4:
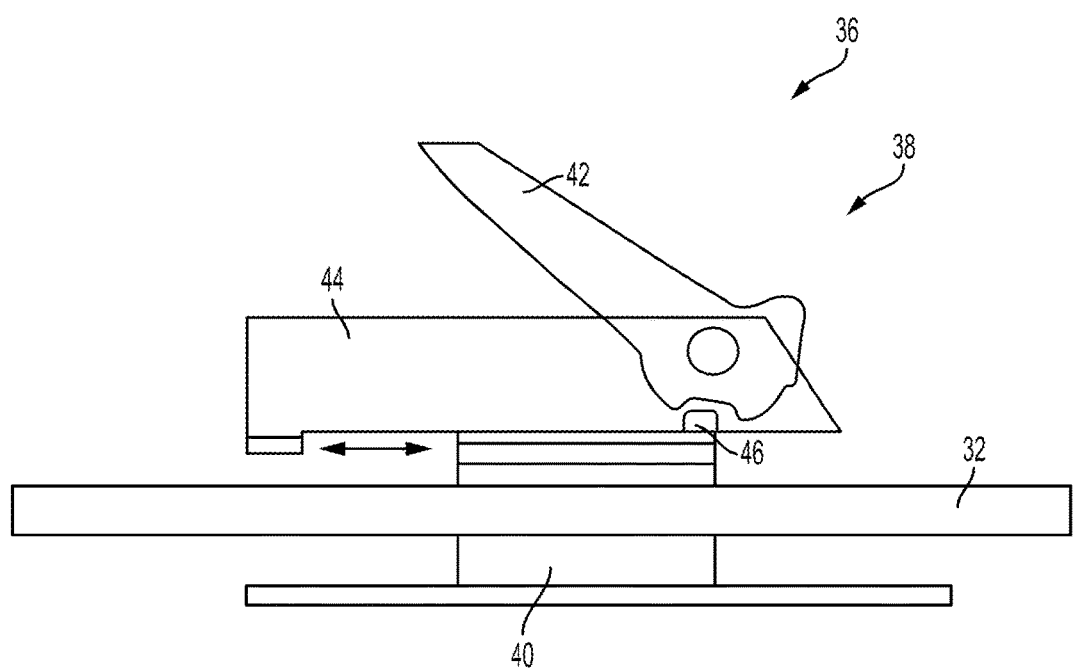
FIG. 4 is a partial side schematic view of one embodiment of an end effector having a knife actuation assembly.

FIG. 4 illustrates a portion of the end effector 36, which has a cutting element actuation assembly 38 that includes a drive member 40, a cutting element 42 in the form of a knife, a sled 44, and the lower rotary driver 32. The drive member 40 includes internal threads that are threadably coupled with the lower rotary driver 32, which is in the form of a lead screw in this illustrated embodiment. Such coupling can allow drive member 40 to move along the lower rotary driver 32 when the lower rotary driver 32 is rotated. As discussed above, the lower rotary driver 32 can be actuated, e.g., via input from a tool driver coupled to the tool's housing, thereby causing rotation of the lower rotary driver 32 and linear movement of the sled 44 along the lower rotary driver 32. The cutting element actuation assembly 38 is configured to orient the cutting element 42 in a cutting position when the drive member 40 pushes the sled 44 distally along the lower rotary driver 32 and to stow the cutting element 42 when the drive member 40 is moved proximally relative to the sled 44. In operation, the lower rotary driver 32 can be rotated to advance the drive member 40 distally along the lower rotary driver 32, thereby pushing the sled 44 in a distal direction and angularly orienting the cutting element 42 in the cutting position. At the end of the distal movement of the assembly 38, the direction of rotation of the lower rotary driver 32 is reversed to retract the drive member 40 proximally relative to the sled 44, thereby causing the cutting element 42 to rotate down into the stowed position, such as via interaction between an interface feature 46 and the cutting element 42.

Figure 5:
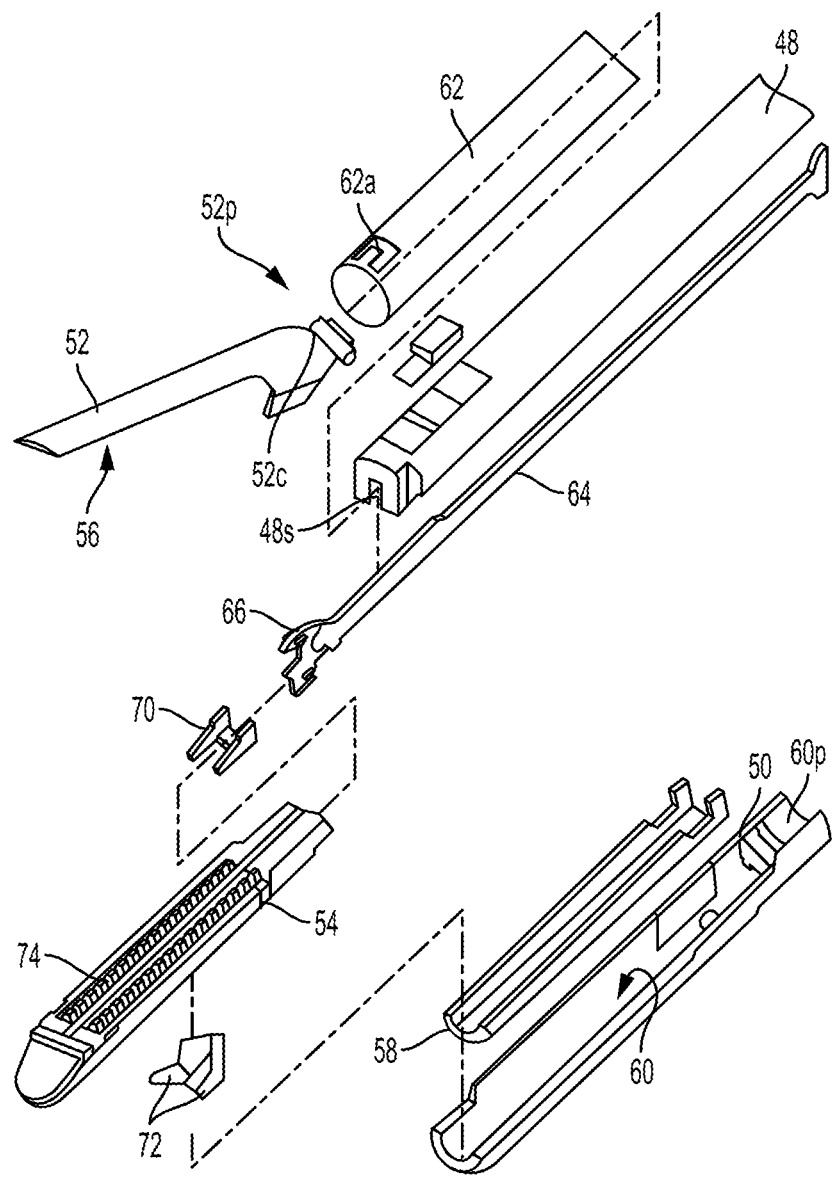
FIG. 5 is an exploded view of a distal portion of another embodiment of a surgical tool.

In at least some embodiments, the surgical tool 10 of FIG. 1 can be a stapler, as mentioned above. FIG. 5 illustrates a distal portion of one embodiment of a surgical stapling tool. The stapler includes an elongate shaft 48 and an end effector at a distal end of the shaft 48. A tool housing (not shown) is at a proximal end of the shaft 48, as discussed herein. The end effector in this illustrated embodiment includes opposed lower and upper jaws 50,52. The lower jaw 50 includes a staple channel configured to support a staple cartridge 54, and the upper jaw 52 has an anvil surface 56 that faces the lower jaw 50 and is configured to operate as an anvil to help deploy staples of the staple cartridge 54 (the staples are obscured in FIG. 5). At least one of the lower and upper jaws 50, 52 is moveable relative to the other of the lower and upper jaws 50, 52 to clamp tissue and/or other objects disposed therebetween. In at least some embodiments, one of the lower and upper jaws 50, 52 can be fixed or otherwise immovable. In some other embodiments, both of the lower and upper jaws 50, 52 be movable. Components of a firing system can be configured to pass through at least a portion of the end effector to eject the staples into the clamped tissue. A cutting element 59 (see FIG. 6), which is a knife blade in this illustrated embodiment, can be associated with the firing system to cut tissue during a stapling procedure.

In this illustrated embodiment, the lower jaw 50 serves as a cartridge assembly or carrier, and the upper jaw 52 serves as an anvil. The staple cartridge 54, having a plurality of staples therein, is supported in a staple tray 58, which in turn is supported within a cartridge channel 60 of the lower jaw 50. The upper jaw 52 has a plurality of staple forming pockets (not shown), each of which is positioned above a corresponding staple from the plurality of staples contained within the staple cartridge 54. The upper jaw 52 can be connected to the lower jaw 50 in a variety of ways. In the illustrated implementation the upper jaw 52 has a proximal pivoting end 52p that is pivotally received within a proximal end 60p of the staple channel 60, just distal to its engagement to the shaft 48. When the upper jaw 52 is pivoted downwardly, the upper jaw 52 moves the anvil surface 56 and the staple forming pockets formed thereon move toward the opposing staple cartridge 54.

Various clamping components can be used to effect opening and closing of the jaws 50, 52 to selectively clamp tissue therebetween. As illustrated, the pivoting end 52p of the upper jaw 52 includes a closure feature 52c distal to its pivotal attachment with the cartridge channel 60. Thus, a closure tube 62, whose distal end includes a horseshoe aperture 62a that engages the closure feature 52c, selectively imparts an opening motion to the upper jaw 52 during proximal longitudinal motion and a closing motion to the upper jaw 52 during distal longitudinal motion of the closure tube 62 in response to input from the tool driver operatively coupled thereto. As mentioned above, the opening and closure of the end effector may be effected by relative motion of the lower jaw 50 with respect to the upper jaw 52, relative motion of the upper jaw 52 with respect to the lower jaw 50, or by motion of both jaws 50, 52 with respect to one another.

Figure 6:
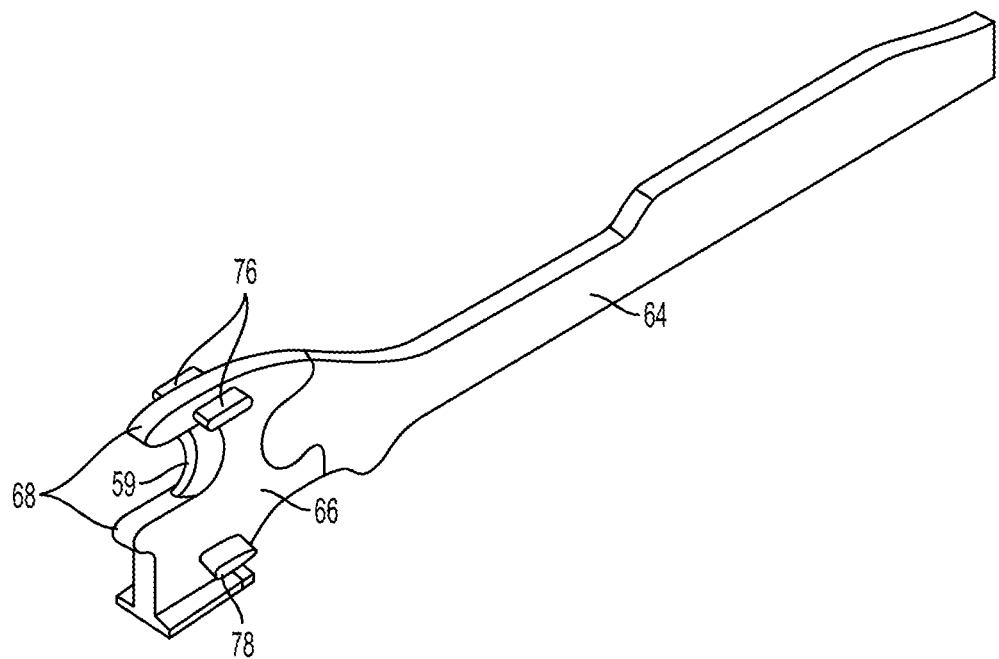
FIG. 6 is a perspective view of a firing bar of the surgical tool of FIG. 5, the firing bar having an E-beam at a distal end thereof.

The firing components of the illustrated embodiment includes a firing bar 64, shown in FIGS. 5 and 6, which has an E-beam 66 on a distal end thereof. The firing bar 64 is flexible in at least a distal portion thereof to facilitate bending of the firing bar 64 at the joint where the end effector is articulated. The firing bar 64 is disposed within the shaft 48, for example in a longitudinal firing bar slot 48s of the shaft 48, and guided by a firing input received by the stapler from a tool driver coupled thereto. The firing input can cause distal motion of the E-beam 66 through at least a portion of the end effector to thereby cause the firing of staples contained within the staple cartridge 54. As in this illustrated embodiment, guides 68 projecting from a distal end of the E-Beam 66 can engage a sled 70, which in turn can push staple drivers 72 upwardly through staple cavities 74 formed in the staple cartridge 54. Upward movement of the staple drivers 72 applies an upward force on each of the plurality of staples within the cartridge 54 to thereby push the staples upwardly against the anvil surface 56 of the upper jaw 52 and create formed staples.

In addition to causing the firing of staples, the E-beam 66 can be configured to facilitate closure of the jaws 50, 52, spacing of the upper jaw 52 from the staple cartridge 54, and/or cutting of tissue captured between the jaws 50, 52. In particular, a pair of top pins 76 and a pair of bottom pins 78 (one of the bottom pins 78 is obscured in FIG. 6) can engage one or both of the upper and lower jaws 50, 52 to compress the jaws 50, 52 toward one another as the firing bar 64 advances distally through the end effector. Simultaneously, the cutting element 59 can be configured to cut tissue captured between the jaws 50, 52.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 7:
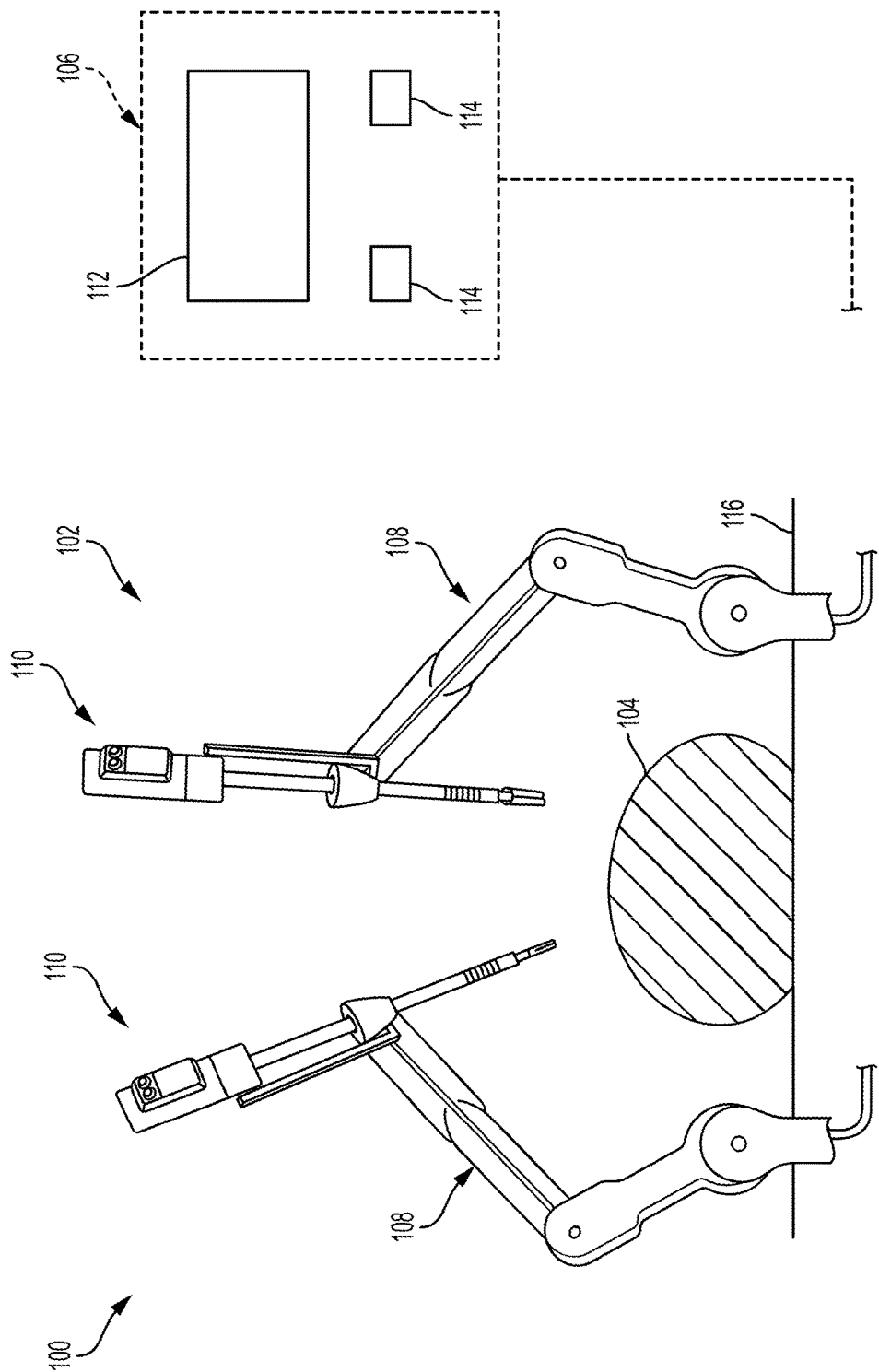
FIG. 7 is a perspective view of one embodiment of a robotic surgical system that includes a patient-side portion and a user-side portion.

FIG. 7 is a perspective view of one embodiment of a robotic surgical system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each tool assembly 110 during a surgical procedure.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

The patient-side portion 102 can have a variety of configurations. As illustrated in FIG. 7, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 7). Alternatively, the patient-side portion 102 can include a single assembly that includes one or more robotic arms 108 extending therefrom.

Figure 8:
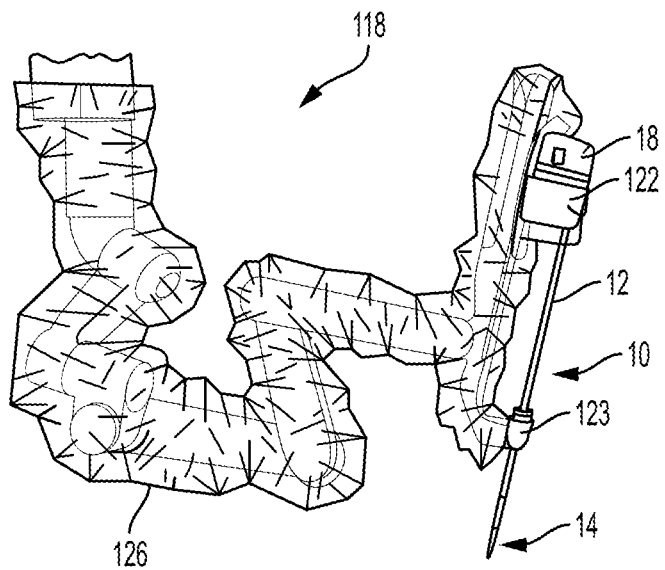
FIG. 8 is a perspective view of one embodiment of a robotic arm of a robotic surgical system with the surgical tool of FIG. 1 releasably and replaceably coupled to the robotic arm.

FIG. 8 illustrates another embodiment of a robotic arm 118 and the surgical tool 10 of FIG. 1 releasably and replaceably coupled to the robotic arm 118. Other surgical instruments can instead be coupled to the arm 118, as discussed herein. The robotic arm 118 is configured to support and move the associated tool 10 along one or more degrees of freedom (e.g., all six Cartesian degrees of freedom, five or fewer Cartesian degrees of freedom, etc.).

The robotic arm 118 can include a tool driver 122 at a distal end of the robotic arm 118, which can assist with controlling features associated with the tool 10. The robotic arm 118 can also include an entry guide 123 (e.g., a cannula mount, cannula, etc.) that can be a part of or releasably and replaceably coupled to the robotic arm 118, as shown in FIG. 8. A shaft of a tool assembly can be inserted through the entry guide 123 for insertion into a patient, as shown in FIG. 8 in which the shaft 12 of the tool 10 of FIG. 1 is shown inserted through the entry guide 123.

In order to provide a sterile operation area while using the surgical system, a barrier 126 can be placed between the actuating portion of the surgical system (e.g., the robotic arm 118) and the surgical instruments coupled thereto (e.g., the tool 10, etc.). A sterile component, such as an instrument sterile adapter (ISA), can also be placed at the connecting interface between the tool 10 and the robotic arm 118. The placement of an ISA between the tool 10 and the robotic arm 108 can ensure a sterile coupling point for the tool 10 and the robotic arm 118. This permits removal of surgical instruments from the robotic arm 118 to exchange with other surgical instruments during the course of a surgery without compromising the sterile surgical field.

Figure 9:
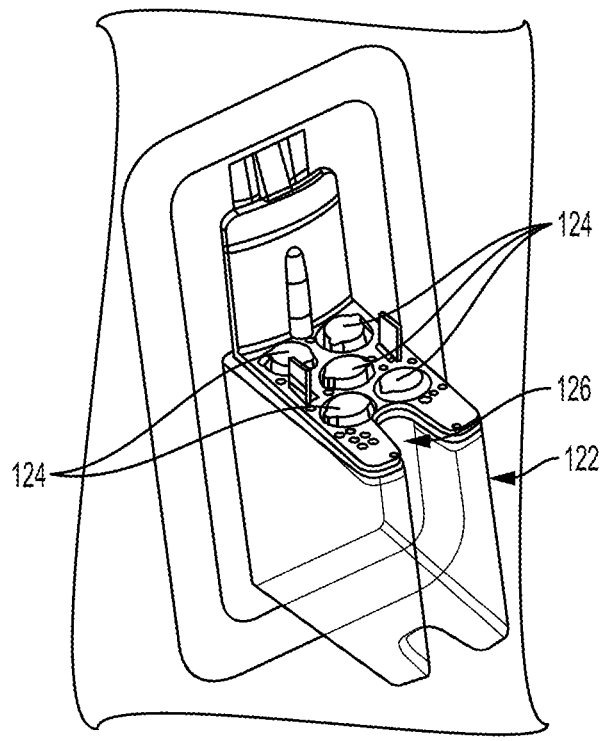
FIG. 9 is a perspective view of a tool driver of the robotic arm of FIG. 8.

FIG. 9 illustrates the tool driver 122 in more detail. As shown, the tool driver 122 includes one or more motors, e.g., five motors 124 are shown, that control a variety of movements and actions associated with the tool 10 coupled to the arm 118. For example, each motor 124 can couple to and/or interact with an activation feature (e.g., gear) associated with the tool 10 for controlling one or more actions and movements that can be performed by the tool 10, such as for assisting with performing a surgical operation. The motors 124 are accessible on the upper surface of the tool driver 122, and thus the tool 10 (e.g., the housing 18 thereof) is configured to mount on top of the tool driver 122 to couple thereto. Exemplary embodiments of motor operation and components of a tool housing (also referred to as a "puck") configured to controlled by tool driver motors are further described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, which is hereby incorporated by reference in its entirety.

The tool driver 122 also includes a shaft-receiving channel 126 formed in a sidewall thereof for receiving the shaft 12 of the tool 10. In other embodiments, the shaft 12 can extend through on opening in the tool driver 122, or the two components can mate in various other configurations.

As mentioned above, a surgical tool, such as the tool 10 of FIG. 1, the tool of FIG. 3, the tool of FIG. 5, or other surgical tool, can be configured to have a corrective force applied thereto that counteracts a torque force experienced by the end effector due to translation of a cutting element therealong. As also mentioned above, a robotic surgical system, such as the robotic surgical system 100 of FIG. 7 or other robotic surgical system, coupled to the surgical tool can be configured to deliver the corrective force to the surgical tool, e.g., a tool driver of the robotic surgical system providing a force to a tool housing of the surgical tool. The robotic surgical system (e.g., a control system thereof that includes a controller and/or a computer system including a controller) can be configured to determine an amount of the corrective force to apply.

Figure 10:
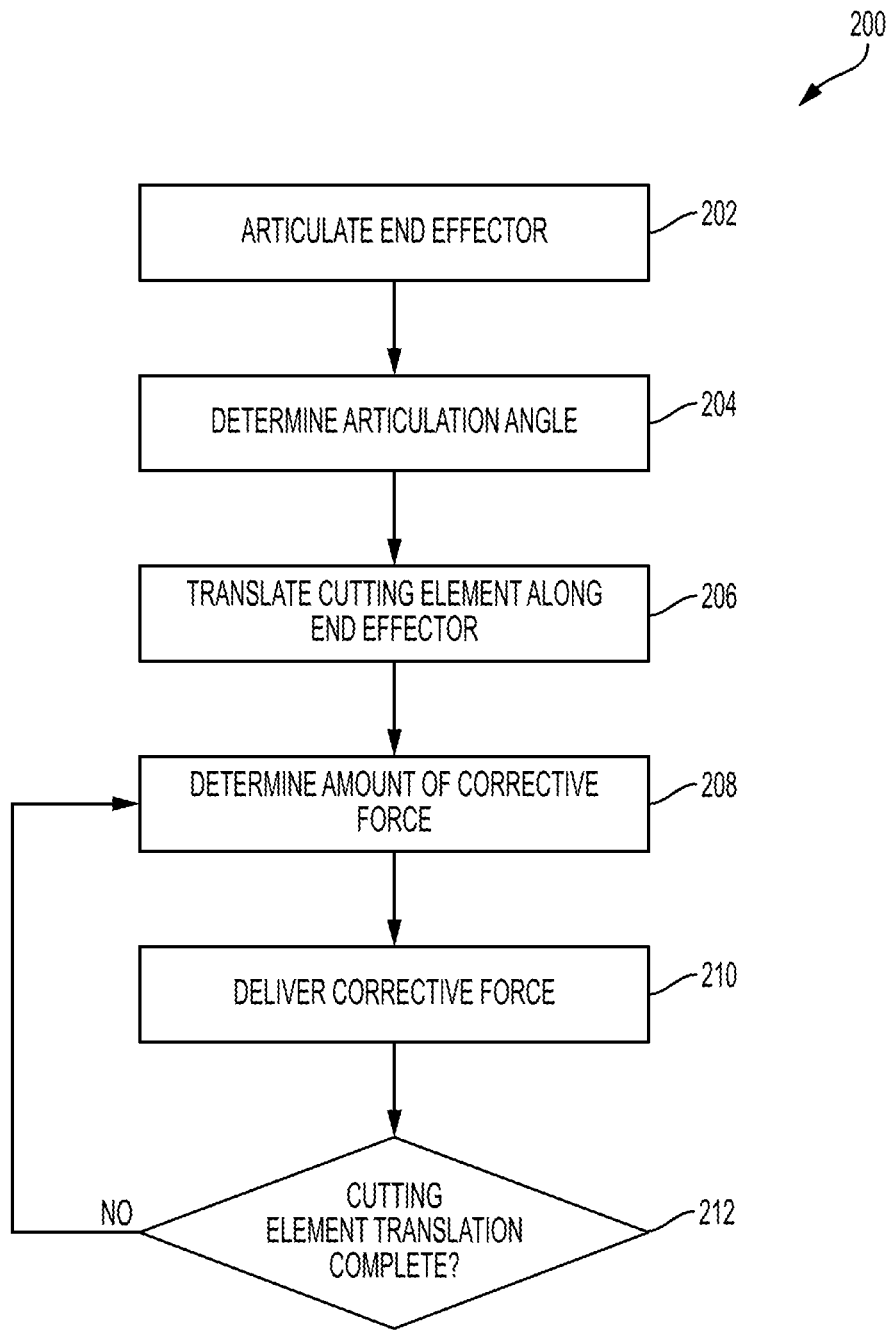
FIG. 10 is a flowchart of one embodiment of a method of applying a corrective force to a surgical tool.
Figure 11:
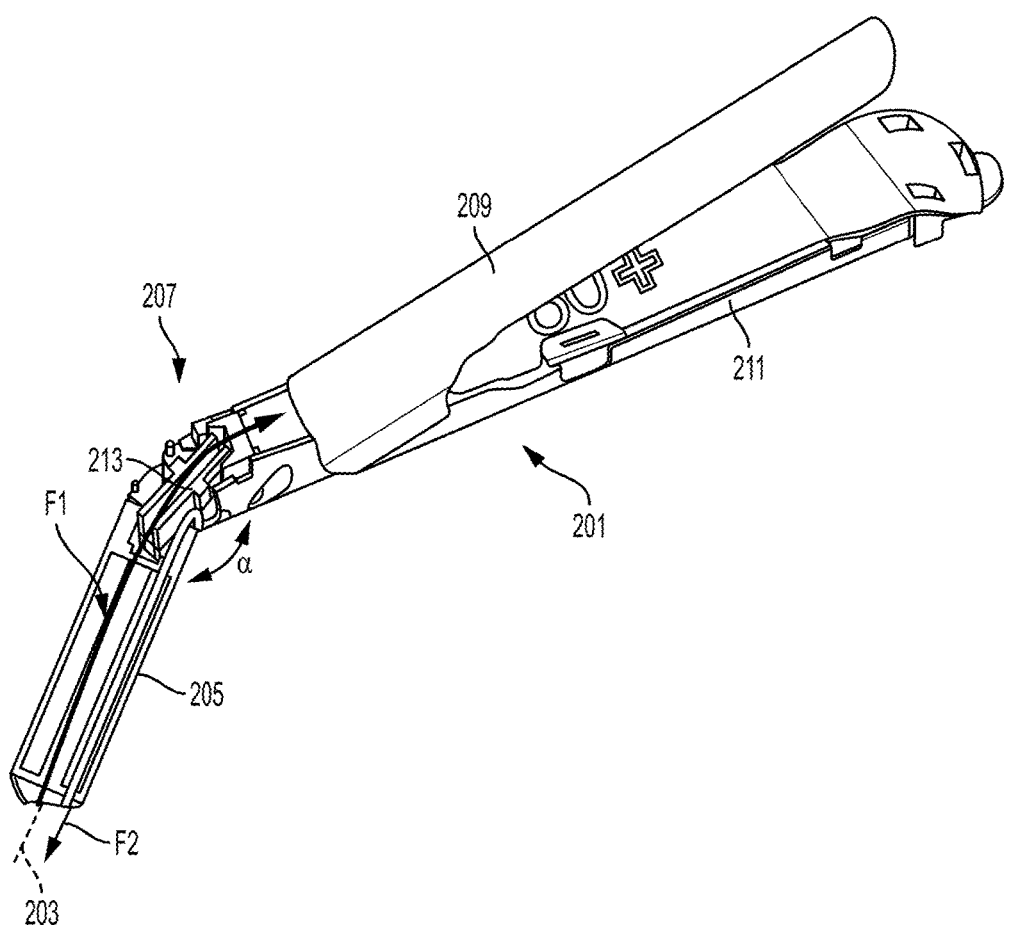
FIG. 11 is a perspective view of one embodiment of a surgical tool having a corrective force applied thereto during cutting element translation.

FIG. 10 illustrates one embodiment of a method 200 of applying a corrective force to a surgical tool during cutting element translation. The method 200 is described for ease of description with reference to the robotic surgical system 100 of FIG. 7 and a surgical tool of FIG. 11 but can be similarly implemented using other embodiments of robotic surgical systems and surgical tools. The surgical tool of FIG. 11 is, for purposes of the description of the method 200, releasably coupled to the robotic surgical system, e.g., a tool housing (not shown) of the surgical tool is releasably coupled to the tool driver 122.

An end effector 201 of the surgical tool can be articulated 202 to be positioned at a non-zero angle α relative to a longitudinal axis 203 of an elongate shaft 205 having the end effector 201 at a distal end thereof. The illustrated angle α is an example angle, with the end effector 201 being configured to articulate at other angles greater than and less than the illustrated angle α. FIG. 11 shows the end effector 201 articulated at the non-zero angle α. The end effector's articulation can be effected in a variety of ways, as discussed herein, such as by the robotic surgical system 100 driving one or more actuation shafts of the surgical tool that are operatively coupled to the end effector 201 and the tool driver 122. The end effector 201 is coupled to the shaft 205 at a wrist or joint 207, at which the end effector 201 is angled relative to the shaft 205. The end effector 201 includes opposed upper and lower jaws 209, 211 configured open and close similar to other embodiments of jaws described herein.

The robotic surgical system 100 can determine 204 the articulation angle α in any of a variety of ways. For example, the robotic surgical system 100, e.g., the control system 114 thereof, can include a computer system with a memory having stored therein data correlating articulation forces with articulation angles. The amount of articulation force delivered to the surgical tool to articulate the end effector 201 is known by the robotic surgical system 100, and the robotic surgical system 100 (e.g., a controller of the control system 114) can use the stored data to look up the articulation angle corresponding to the delivered amount of force, which is the angle α. For another example, the surgical tool can include at least one position sensor configured to sense a position of the end effector 201 that is indicative of the angle α. The at least one position sensor can be configured to communicate the sensed position to the robotic surgical system 100 (e.g., to the control system 114) via the tool driver 122.

With the end effector 201 articulated at the angle α, a cutting element (obscured in FIG. 11) can be translated 206 along the end effector 201 in a distal direction to cut tissue (not shown) engaged by the end effector 201, e.g., tissue clamped between the jaws 209, 211. In this illustrated embodiment, a firing bar 213 having the cutting element thereon, similar to the firing bar 64 and cutting element 59 of FIG. 6, is translated 206 distally along the end effector 201 to cut the tissue. The firing bar 213 is bent at the wrist 207 during the translation of the cutting element, as shown in FIG. 11, and exerts a torque force in a distal direction, which is shown by arrow F1 in FIG. 11. The torque force urges the end effector 201 from its articulated angle α, as discussed above.

Figure 12:
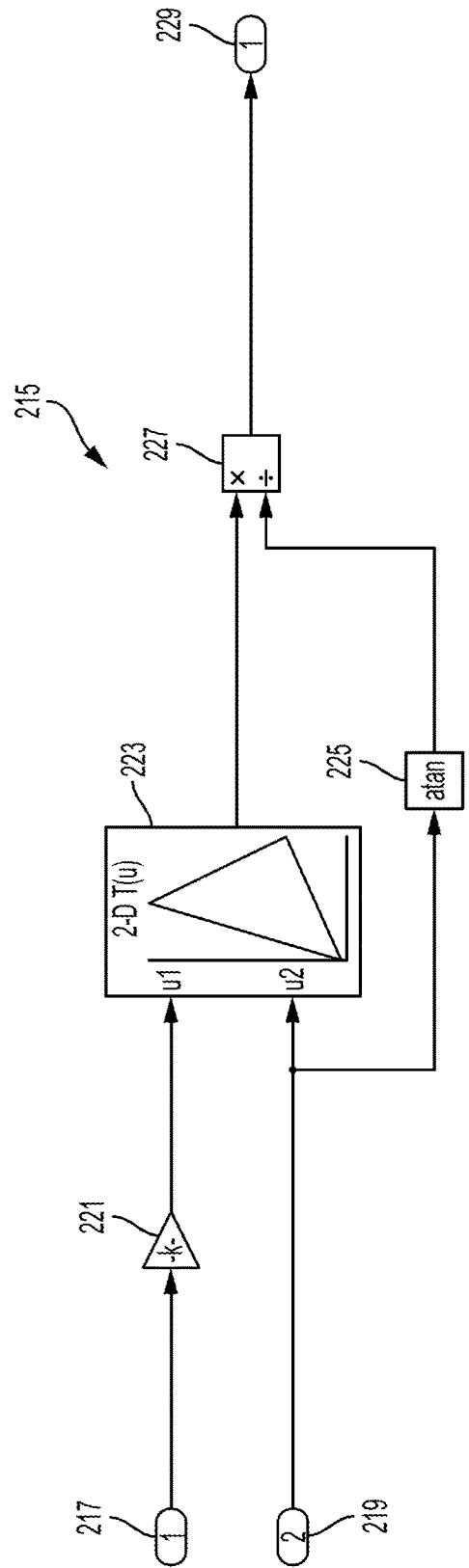
FIG. 12 is a diagram of one embodiment of a method of determining an amount of corrective force.

The robotic surgical system 100, e.g., the controller of the control system 114, can determine 208 an amount of corrective force to deliver to the end effector 201, e.g., deliver via the tool driver 122 to the tool housing, to correct for the torque force. The corrective force can be determined 208 in any of a variety of ways. FIG. 12 illustrates one embodiment of a determination process 215 that the robotic surgical system 100 (e.g., the controller of the control system 114) can implement to determine 208 the amount of corrective force. The process 215 can be stored at the robotic surgical system 100 (e.g., in the memory of the control system 114) for execution thereby (e.g., by the control system's controller).

An amount of torque force applied by the robotic surgical system 100 to the surgical tool to cause the cutting element translation (e.g., firing bar 213 translation) is a first input 217 to the process 215, and the determined 204 articulation angle α is a second input 219 to the process 215. The amount of torque force applied by the robotic surgical system 100 to the surgical tool to cause the cutting element translation can be determined in any of a variety of ways. For example, the torque force can be measured via motor torque, e.g., torque of the motor at the tool driver 122 providing the force to the surgical tool's tool housing. For another example, the robotic surgical system 100 can include at least one force sensor (e.g., at the tool driver 122 adjacent a motor thereat) configured to sense the torque force.

The first input 217 is used to determine 221 a force that the cutting element (e.g., the firing bar 213) is exerting on the end effector 201. The determination 221 can be made, for example, by the robotic surgical system 100 (e.g., the controller of the control system 114) using a lookup table that correlates each torque force that the robotic surgical system can deliver to a force that the torque force causes to be exerted on the end effector 201. The lookup table can be stored at the robotic surgical system 100 (e.g., in the memory of the control system 114). The determined 221 force is input into a 2-D lookup table 223. The second input 219 is also input into the 2-D lookup table 223. The robotic surgical system 100 (e.g., the controller of the control system 114) uses the 2-D lookup table 223 and the two inputs thereto to determine a torque force at the wrist 207. In other words, the 2-D lookup table 223 can correlate torque forces at the wrist 207 to different end effector articulation angles and different torque forces exerted on the end effector, with a one of the torque forces matching the two inputs to the 2-D lookup table 223 being the output of the lookup table 223 function that is indicative of the torque force at the wrist 207. The data (e.g., predetermined forces) in the lookup table 223 can be gathered, for example, through experiments and/or through historical use of the surgical tool.

The robotic surgical system 100 (e.g., the controller of the control system 114) also calculates 225 an inverse tangent (arc tangent or a tan) of the second input 219.

The robotic surgical system 100 (e.g., the controller of the control system 114) divides 227 the torque force at the wrist 207, e.g., the output from the lookup table 223, by the calculated 225 inverse tangent to obtain a result 229. The result 229 is the amount of corrective force for the robotic surgical system 100 to apply to the end effector 201 to counteract the torque force, e.g., the force shown by arrow F1 in FIG. 11.

Having determined 208 the amount of corrective force, the robotic surgical system 100 delivers 210 the corrective force to the surgical tool, e.g., by the tool driver 122 imparting torque to one or more actuation shafts of the surgical tool. The corrective force is in an opposite direction to the torque force. In others words, the torque force is in the distal direction, as shown by arrow F1, and the corrective force is in a proximal direction, as shown by arrow F2 in FIG. 11. The corrective force may thus substantially cancel out the urging of the end effector's movement caused by the cutting element's translation along the end effector 201 to maintain the end effector 201 at the articulation angle α during the cutting element's translation. A person skilled in the art will appreciate that the corrective force may not precisely cancel out the torque force exerted during cutting element translation but nevertheless be configured to substantially cancel out the torque force due to any number of factors, such as sensitivity of measurement equipment.

As in this illustrated embodiment, throughout the cutting element's translation the robotic surgical system 100 can repeatedly determine 208 the amount of corrective force and deliver 210 the determined 208 amount in an iterative process. This iterative process may help account for changes in applied motor torque that may occur during the cutting element's translation, such as if motor torque is increased to help move the cutting element through thicker and/or tougher tissue. In other embodiments, the process 200 may end after the corrective force 210 is delivered 210 once, which may help conserve processing resources.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 13:
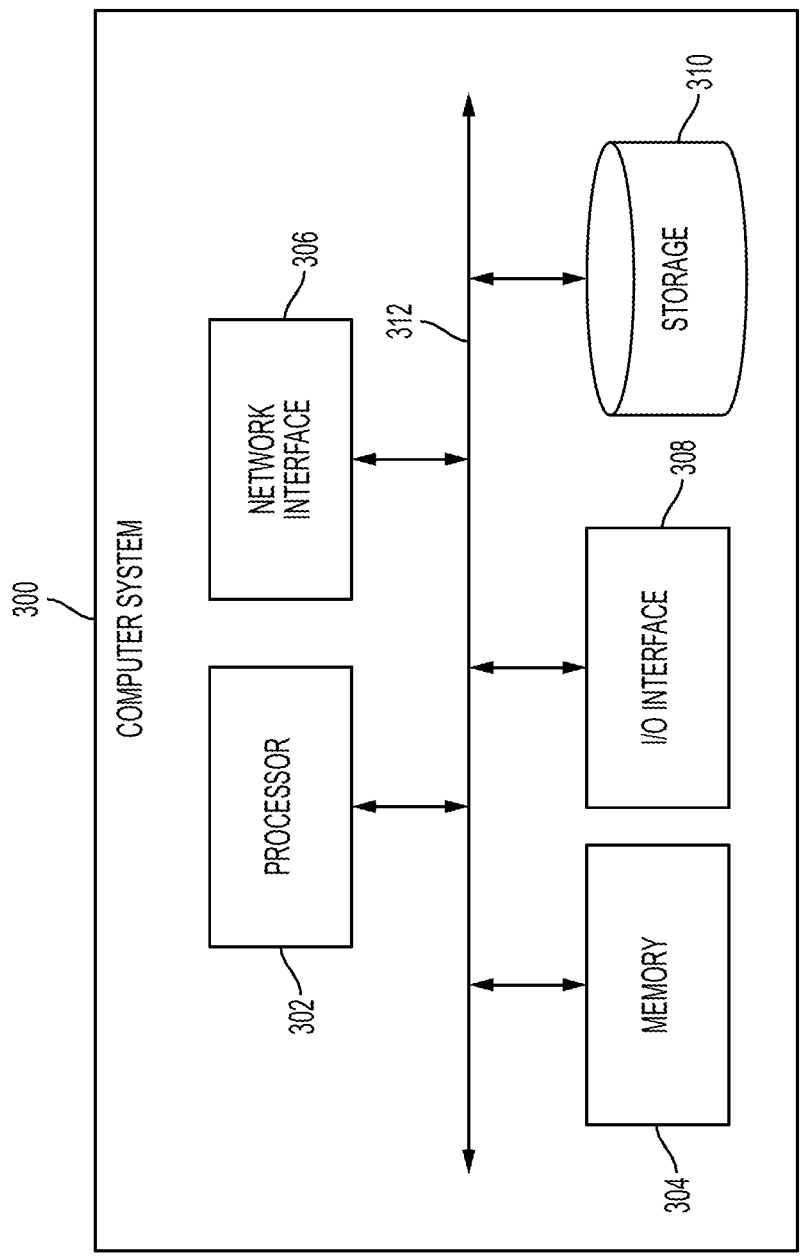
FIG. 13 is a schematic view of one embodiment of a computer system.

FIG. 13 illustrates one exemplary embodiment of a computer system 300. As shown, the computer system 300 includes one or more processors 302 which can control the operation of the computer system 300. "Processors" are also referred to herein as "controllers." The processor(s) 302 can include any type of microprocessor or central processing unit (CPU), including programmable general-purpose or special-purpose microprocessors and/or any one of a variety of proprietary or commercially available single or multi-processor systems. The computer system 300 can also include one or more memories 304, which can provide temporary storage for code to be executed by the processor(s) 302 or for data acquired from one or more users, storage devices, and/or databases. The memory 304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 300 can be coupled to a bus system 312. The illustrated bus system 312 is an abstraction that represents any one or more separate physical busses, communication lines/interfaces, and/or multi-drop or point-to-point connections, connected by appropriate bridges, adapters, and/or controllers. The computer system 300 can also include one or more network interface(s) 306, one or more input/output (IO) interface(s) 308, and one or more storage device(s) 310.

The network interface(s) 306 can enable the computer system 300 to communicate with remote devices, e.g., other computer systems, over a network, and can be, for non-limiting example, remote desktop connection interfaces, Ethernet adapters, and/or other local area network (LAN) adapters. The IO interface(s) 308 can include one or more interface components to connect the computer system 300 with other electronic equipment. For non-limiting example, the IO interface(s) 308 can include high speed data ports, such as universal serial bus (USB) ports, 1394 ports, Wi-Fi, Bluetooth, etc. Additionally, the computer system 300 can be accessible to a human user, and thus the IO interface(s) 308 can include displays, speakers, keyboards, pointing devices, and/or various other video, audio, or alphanumeric interfaces. The storage device(s) 310 can include any conventional medium for storing data in a non-volatile and/or non-transient manner. The storage device(s) 310 can thus hold data and/or instructions in a persistent state, i.e., the value(s) are retained despite interruption of power to the computer system 300. The storage device(s) 310 can include one or more hard disk drives, flash drives, USB drives, optical drives, various media cards, diskettes, compact discs, and/or any combination thereof and can be directly connected to the computer system 300 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 13 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 300 can also include a web server for generating and/or delivering the web pages to client computer systems.

In an exemplary embodiment, the computer system 300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
a surgical tool including an elongate shaft having an end effector at a distal end thereof, the surgical tool including a rod configured to move to selectively orient the end effector at an angle relative to the elongate shaft, the movement of the rod being configured to be driven by a motor providing a torque force to the surgical tool; and
a controller configured to determine an amount of corrective force based on the angle and the torque force, and the controller being configured to apply the determined corrective force to the rod.

2. The system of claim 1, wherein the surgical tool includes a cutting element configured to translate along the end effector to cut tissue engaged by the end effector, and the controller is configured to cause the determined corrective force to be applied to the rod during the translation of the cutting element.

3. The system of claim 1, further comprising a memory storing a lookup table therein, the lookup table correlating each of a plurality of articulation angles and a plurality of motor torque forces to corrective forces to apply to the rod, and the controller being configured to determine the amount of corrective force via the lookup table.

4. The system of claim 1, wherein the controller is configured to determine the angle at which the end effector is angularly oriented relative to the elongate shaft.

5. The system of claim 1, wherein the end effector is configured to pivot at a joint relative to the elongate shaft to effect the angular orientation of the end effector relative to the elongate shaft, the rod extending through the joint.

6. The system of claim 1, wherein the controller is included in a robotic surgical system configured to releasably couple to the surgical tool.

7. The system of claim 1, further comprising a tool driver of a robotic surgical system that includes the motor, the surgical tool being configured to releasably operatively couple to the tool driver.

8. The system of claim 7, wherein the robotic surgical system includes the controller, the controller being in operative communication with the tool driver.

9. The system of claim 1, wherein the surgical tool includes a cutting element configured to translate along the end effector to cut tissue engaged by the end effector, the surgical tool includes a driver configured to be driven to rotate by the motor, and the rotation of the driver is configured to cause the translation of the cutting element along the end effector.

10. A surgical system, comprising:
a surgical tool including an elongate shaft, an end effector coupled to a distal end of the elongate shaft, a cutting element configured to translate along the end effector to cut tissue engaged by the end effector, and a rod configured to move to articulate the end effector at an angle relative to the elongate shaft in response to a first force provided to the surgical tool by a robotic surgical system configured to releasably couple to the surgical tool; and
a controller configured to cause adjustment of the first force provided to the surgical tool by the robotic surgical system during the translation of the cutting element and thereby counteract a second force caused by the translation of the cutting element along the end effector.

11. The system of claim 10, wherein the cutting element is configured to translate along the end effector in response to a third force provided to the surgical tool by the robotic surgical system, and the controller is configured to determine an amount of the adjustment of the first force based on the third force and on the angle at which the end effector is articulated relative to the elongate shaft.

12. The system of claim 11, further comprising a memory storing a lookup table therein that correlates amounts of the second force to each of a plurality of angles at which the end effector can be articulated relative to the elongate shaft and each of a plurality of third forces that can be provided to the surgical tool by the robotic surgical system to cause the translation of the cutting element, and the controller determining the amount of the adjustment of the first force includes looking up in the lookup table the angle at which the end effector is articulated relative to the elongate shaft and looking up in the lookup table the third force being provided to the surgical tool by the robotic surgical system.

13. The system of claim 10, further comprising a memory storing a lookup table therein, the controller being configured to access the lookup table and thereby determine an amount of the adjustment of the first force.

14. The system of claim 10, wherein the robotic surgical system includes a motor configured to provide the first force to the surgical tool.

15. The system of claim 10, wherein the controller is included in the robotic surgical system.

16. A surgical method, comprising:
applying an amount of force to a surgical tool and thereby cause an end effector of the surgical tool to articulate at an angle relative to an elongate shaft having the end effector at a distal end thereof;
with the end effector articulated, causing a cutting element to translate along the end effector; and
during the translation of the cutting element, changing the amount of force being applied to the surgical tool while maintaining the angle at which the end effector is articulated relative to the elongate shaft.

17. The method of claim 16, wherein the translation of the cutting element along the end effector exerts a second amount of force on the surgical tool, and changing the amount of force being applied to the surgical tool counteracts the second amount of force to allow the surgical tool to maintain the angle at which the end effector is articulated relative to the elongate shaft.

18. The method of claim 16, wherein the translation of the cutting element is caused by applying a second amount of force to the surgical tool, and the amount of force being applied to the surgical tool is changed based on the angle at which the end effector is articulated relative to the elongate shaft and based on the second amount of force being applied to the surgical tool.

19. The method of claim 18, wherein the surgical tool is releasably and replaceably coupled to a robotic surgical system, and the robotic surgical system applies the amount of force to the surgical tool and applies the second amount of force to the surgical tool.

20. The method of claim 16, wherein the surgical tool is releasably and replaceably coupled to a robotic surgical system, and the robotic surgical system applies the amount of force to the surgical tool and changes the amount of force being applied to the surgical tool.

* * * * *